United States Patent [19]

Wilson, Jr. et al.

[11] Patent Number: 4,562,291

[45] Date of Patent: Dec. 31, 1985

[54] OLIGOMERIZATION OF ALKYL GROUPS ON AMINES

[75] Inventors: Robert B. Wilson, Jr., Mountainview; Richard M. Laine, Palo Alto, both of Calif.

[73] Assignee: Air Products and Chemicals, Inc., Allentown, Pa.

[21] Appl. No.: 683,531

[22] Filed: Dec. 19, 1984

[51] Int. Cl.$^4$ ............................................. C07C 85/00
[52] U.S. Cl. ................................................... 564/463
[58] Field of Search .......................................... 564/463

[56] References Cited

U.S. PATENT DOCUMENTS

| | | | |
|---|---|---|---|
| 3,726,925 | 4/1973 | Fenton | 564/469 |
| 4,096,150 | 6/1978 | Berthoux et al. | 564/463 |
| 4,322,530 | 3/1982 | Jachimowicz | 544/403 |
| 4,430,513 | 2/1984 | Homeier | 564/469 |

FOREIGN PATENT DOCUMENTS

| | | | |
|---|---|---|---|
| 26071 | 4/1981 | European Pat. Off. | 564/463 |
| 24203 | 3/1975 | Japan | 564/463 |

OTHER PUBLICATIONS

Fine Chemicals Patents Journal (8), No. 6, German, 5:2–5:3 (2/12/68).

Primary Examiner—Charles F. Warren
Assistant Examiner—R. A. Picard
Attorney, Agent, or Firm—Rodgers, Mark L.; E. Eugene Innis; James C. Simmons

[57] ABSTRACT

Long chain alkylamines are synthesized by the oligomerization of shorter chain alkylamines at a temperature between 50°–250° C. and a pressure between 1–300 atmospheres in the presence of a catalyst mixture comprising a fluoroborate salt and a ruthenium, an osmium, or an iridium compound.

17 Claims, No Drawings

OLIGOMERIZATION OF ALKYL GROUPS ON AMINES

TECHNICAL FIELD

The present invention relates to the catalytic synthesis of longer chain alkyl amines by the oligomerization of mono-, di- and trialkylamines.

BACKGROUND OF THE INVENTION

One common method of alkylating organic compounds is by utilizing alkylating agents such as olefins or alkylhalides in the presence of a Friedel Crafts catalyst. One example of alkylating an amine compound using an olefin is described in U.S. Pat. No. 4,322,530. This patent teaches a one-step catalytic method of alkylating a polyamine by contacting a compound having a multiplicity of primary and/or secondary amine groups, a monoolefin, water and carbon monoxide. These components are contacted in the presence of a catalytic amount of a rhodium compound selected from metallic rhodium, rhodium salts, oxides, or carbonyls, which may have phosphines or other ligands present. The reaction is carried out in an inert solvent at temperatures from 50° to 250° C. and pressures from about 30 to 300 atmospheres.

Using an alkylamine as the alkylating agent generally proved to be unfeasible in that the rate of production of the desired alkylated product proceeded at a low rate which slowed, or in some instances, ceased to operate. The slowness of the reaction is due to the fact that the amine group of the alkylating agent poisons the catalyst by the formation of an acid-base compound, the poison thus rendering the catalyst incapable of performing as such.

U.S. Pat. No. 4,430,513 discloses one method in which alkylamines can satisfactorily be used as alkylating agents. Specifically, this patent teaches the self-alkylation of alkylamine compounds which contain at least two alkyl substituents containing from about 2 to 6 carbon atoms. The alkylamine compounds are alkylated in the presence of a metal carbonyl or a metal compound capable of forming a carbonyl at reaction conditions. The reaction is carried out at temperatures ranging from 50° to 300° C. and at high pressures; i.e., between 20 and 300 atmospheres.

BRIEF SUMMARY OF THE INVENTION

The present invention involves a process for the catalytic synthesis a long chain alkylamines. Specifically, mono-, di- and trialkylamines are oligomerized to form longer chain alkylamines by contacting the mono-, di- or trialkylamine with a catalyst mixture comprising a tetra-fluoroborate salt and a ruthenium, an osmium, or an iridium containing compound in a ratio of between 1:1 to 1:100. The reaction is typically carried out at a temperature between 50° to 250° C. and at a pressure between 1 atm and 18 atm, although pressures as high as 300 atm can be used.

The present invention is superior to the prior art processes, and in particular U.S. Pat. No. 4,430,513, in that by using the catalyst mixture described above, a syngas atmosphere does not have to be maintained during the reaction. Previous catalyst systems required a carbonyl to be formed with the catalyst which necessitates a carbon monoxide-rich atmosphere to be maintained. Additionally, whereas the prior art processes only oligomerize alkylamine compounds which contain at least two alkyl substituents, the present process achieves good oligomerization products using monoalkylamines. These good results can be had even while operating the process at low pressures; e.g., as low as 1 atm.

DETAILED DESCRIPTION OF THE INVENTION

The present invention provides a process for synthesizing long chain alkylamines by self-alkylation or oligomerization of shorter chain alkylamines.

Any typical alkylamine can be oligomerized in accordance with the present invention, with monoethylamine or diethylamine being the preferred reactants. Oligomerization produces a mixture of various longer chain alkylamines.

The reaction is run in the presence of a catalyst mixture comprising a fluoroborate salt and a ruthenium, an osmium, or an irridium containing compound, with $RuCl_3$ being preferred. $NaBF_4$ is the preferred fluoroborate salt with Li, K, Rb, Cs and Ag all being suitable substitutes for Na. The catalyst mixture should be at a fluoroborate to ruthenium compound concentration ratio of between 1:1 to 1:100, with a concentration between about 1:2 to 1:6 being preferred. Unlike the prior art, a CO-rich syngas atmosphere is not required since the formation of a carbonyl with the catalyst is not necessary. While such a syngas atmosphere is not required, operating with one will not adversely affect the reaction and may, in some instances, improve the reaction.

The oligomerization is a liquid phase reaction and is preferably carried out in the presence of an aliphatic amine solvent. Other solvents such as alcohol, ether, aromatics or paraffins are less desirable, as they have been shown to have a detrimental affect on the reaction.

Oligomerization is carried out at a temperature range between 50° and 250° C. with a temperature range between 165° and 220° being preferred. Unlike the prior art, the present process can be run at low pressures; i.e. between 1 and 18 atms, with a range between 1 and 300 atms being operable.

The present process differs from the prior art in that monoalkylamines, and specifically monoethylamines can be oligomerized, whereas prior art processes were only operable for amines having two or more alkyl groups. The present catalyst system eliminates the need for a CO-rich atmosphere, and also allows the reaction to be carried out at lower pressures than heretofore thought possible. One important application of the present process is the production of dibutylamine by the oligomerization of diethylamine since dibutylamine is a valuable product which has wide commercial application, such as use in biocides and surfactants.

The process of the present invention can be better understood by reference to the following examples. These examples are illustrative of the present invention and are not meant to be limiting.

EXAMPLE 1

Several runs were carried out in accordance with the above description. A 34 ml quartz-lined bomb reactor was mixed with 0.1 mmol $RuCl_3$ (anhydrous) 0.6 mmol $AgBF_4$ (anhydrous) or $NaBF_4$ (anhydrous) and 1 ml $Et_2NH$ except where indicated otherwise. The mixture was heated to 190° C. for 24 hours and subsequently analyzed by gaschromatography. The results are reported in Table 1. The Product values represent mole% of that species in solution as determined by gas chromatographic analysis.

ized with $C_2H_4$. It was then heated to 190° for 24 hours and the products were analyzed by gas chromatography. The results was reported in Table 2 below. The product values represent mole% of that species in solution as determined by gas chromatographic analysis.

TABLE 1

| Catalyst System | PRODUCTS | | | | | | | | |
|---|---|---|---|---|---|---|---|---|---|
| | $EtNH_2$ | $Et_2NH$ | $Et_3N$ | BuNHEt | $BuNET_2$ | $Bu_2NH$ | $C_6NHEt$ | $BuNEt_2$ | Remarks |
| Run 1 $RuCl_3/AgBF_4$ | — | 6.2 | 16.3 | 7.1 | 9.3 | 2.1 | 7.3 | 2.0 | |
| Run 2 $RuCl_3/AgBF_4$ | — | 13.2 | 29.1 | 6.8 | 7.8 | 12.4 | 3.1 | 9.6 | Higher oligomers |
| Run 3 $RuCl_3/AgBF_4$ | 1.0 | 8.0 | 28.5 | 24.4 | 1.6 | 3.1 | 7.0 | | |
| Run 4 $RuCl_3/AgBF_4$ | — | 24.2 | trace | | | | | | Tetrahydrofuran |
| Run 5 $RuCl_3/AgBF_4$ | — | 31.2 | trace | | | | | | Benzene |
| Run 6 $RuCl_3/AgBF_4$ | — | 24.2 | trace | | | | | | Pyridine |
| Run 7 $RuCl_3/AgBF_4$ | — | 10.7 | 14.9 | 2.1 | — | 1.5 | 1.6 | 0.8 | Triphenylphosphine |
| Run 8 $RuCl_3/AgBF_4$ | 2.1 | 59.3 | 22.8 | 2.0 | 1.8 | 2.0 | 4.0 | 4.5 | 2 mL $Et_2NH$ |
| Run 9 $RuCl_3/AgBF_4$ | 2.4 | 76.2 | 17.5 | 1.7 | 0.8 | 0.30 | 0.3 | 0.4 | 5 mL $Et_2NH$ |
| Run 10 $RuCl_3/AgBF_4$ | 0.2 | 37.1 | 39.1 | 8.4 | 5.5 | 5.2 | 2.9 | 1.3 | |
| Run 11 $RuCl_3/NaBF_4$ | 0.3 | 45.2 | 34.6 | 4.4 | 3.2 | 3.2 | 4.0 | 4.0 | 1.0 mL $H_2O$ |
| Run 12 $RuCl_3/AgBF_4$ | 0.3 | 85.1 | 9.9 | 1.2 | 0.4 | 0.5 | 0.6 | | 170° C. |
| Run 13 $RuCl_3/AgBF_4$ | 0.8 | 76.8 | 1.6 | 0.8 | 0.7 | 0.5 | 0.7 | 0.3 | 60 psi $NH_3$/ 11% $Me_3$ pyridine |
| Run 14 $RuCl_3/AgBF_4$ | 1.0 | 7.2 | 42.2 | 9.2 | 22.7 | 1.6 | 1.5 | 3.7 | $CF_3CO_2NH_4$ |

Table 1 generally shows that oligomerization of $Et_2NH$ takes place when carried out under the conditions described above. Runs 1 and 3 specifically demonstrate that a solvent other than the reactant is not necessary for the reaction to proceed, while run 1, indicates that the use of an aliphatic amine solvent may increase certain oligomerization products. The reactions proceeded in the runs using a $RuCl_3/AgBF_4$ catalyst mixture as well as in Run 11 where a $RuCl_3/NaBF_4$ mixture was used. Measurable oligomerization products were not observed for runs 4, 5 and 6. This was probably due to utilization of unfavorable solvents. Other runs under various reaction conditions or using different amounts of types of solvents showed varied, but good oligomerization products.

EXAMPLE 2

Several runs were carried out to determine if the oligomerization reaction could be carried out using only one component of the catalyst mixture. 2 ml $Et_2NH$ were mixed with the catalyst in a 34 ml quartz-lined bomb reactor. The reactor was sealed and pressur-

TABLE 2

| Catalyst System | PRODUCTS | | | | | | | |
|---|---|---|---|---|---|---|---|---|
| | $EtNH_2$ | $Et_2NH$ | $Et_3N$ | BuNHEt | $BuNEt_2$ | $Bu_2NH$ | $C_6NHEt$ | $BuNEt_2$ |
| Run 15 $RuCl_3/AgBF_4$ | 2.1 | 59.3 | 22.8 | 2.0 | 1.8 | 2.0 | 4.0 | 4.5 |
| Run 16 $AgBF_4$ only | — | 89.2 | 10.0 | — | — | — | — | — |
| Run 17 $RuCl_3$ only | — | 94.0 | 5.0 | — | — | — | — | — |

Runs 15–17 in Table 2 above clearly indicate that the oligomerization will not take place if only one component of the catalyst mixture is used. Both the $RuCl_3$ (or equivalent compound as listed above), and a fluoroborate salt are necessary for substantial oligomerization to take place.

EXAMPLE 3

Several runs were carried out to determine if, unlike the prior art, monoalkylamines could undergo oligomerization in the presence of the subject catalyst mixture. 0.1 mmol of $RuCl_3$ and 0.3 mmol of $NaBF_4$ or $AgBF_4$ were mixed in a 34 ml quartz-lined bomb reactor. The alkylamine was added and the mixture was heated for 24 hours and subsequently analyzed by gas chromatography. The results are reported in Table 3 below. The product values represent mole% of that species in solution as determined by gas chromatographic analysis.

TABLE 3

| Catalyst System | PRODUCTS | | | | | | | | Remarks |
|---|---|---|---|---|---|---|---|---|---|
| | EtNH$_2$ | Et$_2$NH | Et$_3$N | BuNHEt | BuNET$_2$ | Bu$_2$NH | C$_6$NHEt | Bu$_2$NEt | |
| Run 18 RuCl$_3$/AgBF$_4$ | 0.8 | 15.3 | 55.8 | 5.1 | 12 | 0.8 | 4.0 | 2.0 | Et$_3$N Solvent/3 mL EtNH$_2$ reactant 180° C. |
| Run 19 RuCl$_3$/NaBF$_4$ | 0.6 | 13.3 | 70.6 | 3.1 | 7.1 | 0.3 | 2.0 | 1.0 | Et$_3$N Solvent/3 mL EtNH$_2$ reactant 180° C. |
| Run 20 RuCl$_3$/NaBF$_4$ | — | — | 90.0 | — | — | — | — | — | Et$_3$N only 180° C. |
| Run 21 RuCl$_3$/NaBF$_4$ | 2.9 | 27.7 | 60.9 | 0.5 | 0.6 | — | — | — | Et$_3$N 220° C./ 500 psi H$_2$ |
| Run 22 RuCl$_3$/NaBF$_4$ | 2.5 | 23.9 | 42.7 | 5.5 | 6.9 | 0.42 | 1.0 | 1.23 | Et$_3$N only 220° C. |

The results of Table 3 demonstrate that the present process is capable of oligomerizing EtNH$_2$. It is difficult to run EtNH$_2$ because it is mostly in the gas phase at reaction temperatures and pressures. Et$_3$N was therefore used as a solvent. Runs 18 and 19 showed significant oligomerization of the EtNH$_2$. To demonstrate that it was, in fact, the EtNH$_2$ which underwent oligomerization and not the Et$_3$N solvent, a blank run 20, using only Et$_3$N was carried out under the same conditions as runs 18 and 19. Run 20 at 180° C. showed no evidence of oligomerization or even disproportionation of Et$_3$N into EtNH$_2$ and Et$_2$NH. These results show that, under these conditions, Et$_3$N is practically inert, while EtNH$_2$ undergoes significant oligomerization.

When the reaction temperature was increased to 220° C., runs 21 and 22, oligomerization of Et$_3$N did occur. This shows that Et$_3$N can be used as a reactant for the present process if the reaction conditions are faborable, e.g., at a temperature greater than about 200° C.

Having thus described the present invention, what is now deemed appropriate for Letters Patent is set out in the following appended claims.

What is claimed is:

1. A process for the oligomerization of alkylamines to produce longer carbon chain alkylamines, said process comprising: contacting said alkylamine with a catalyst mixture comprising a tetra-fluoroborate salt and a ruthenium, an osmium, or an iridium containing compound in a ratio of between 1:1 to 1:100 at a temperature between 50° and 250° C. and at a pressure between 1 atm and 300 atm.

2. The process in accordance with claim 1 wherein said tetra-fluoroborate salt is NaBF$_4$.

3. The process in accordance with claim 2 wherein said catalyst mixture comprises NaBF$_4$ and RuCL$_3$ in a ratio between 1:2 and 1:6.

4. The process in accordance with claim 3 wherein said oligomerization is carried out at a temperature between 165° and 220° C.

5. The process in accordance with claim 4 wherein said oligomerization is carried out at a pressure between 1 atm and 18 atm.

6. The process in accordance with claim 5 wherein the ratio of amine to catalyst is about 2000:1.

7. The process in accordance with claim 6 wherein the oligomerization is carried out in an aliphatic amine solvent.

8. The process in accordance with claim 1 wherein the alkylamine to be oligomerized in monoethylamine.

9. The process in accordance with claim 1 wherein the alkylamine to be oligomerized is a trialkylamine.

10. The process in accordance with claim 9 wherein the reaction is carried out at a temperature between 200° and 250° C.

11. A process for the synthesis of dibutylamine by the oligomerization of diethylamine which comprises:
contacting said diethylamine with a catalyst mixture comprising a tetra-fluoroborate salt and a ruthenium, an osmium, or an iridium containing compound in a ratio of between 1:1 to 1:100 at a temperature between 50° and 250° C. and at a pressure between 1 atm and 300 atm.

12. The process in accordance with claim 11 wherein said tetra-fluoroborate salt is NaBF$_4$.

13. The process in accordance with claim 12 wherein said catalyst mixture comprises NaBF$_4$ and RuCl$_3$ in a ratio between 1:2 and 1:6.

14. The process in accordance with claim 13 wherein said oligomerization is carried out at a temperature between 165° and 220° C.

15. The process in accordance with claim 14 wherein said oligomerization is carried out at a pressure between 1 atm and 18 atm.

16. The process in accordance with claim 15 wherein the ratio of diethylamine to catalyst is about 2000:1.

17. The process in accordance with claim 14 wherein the oligomerization is carried out in an aliphatic amine solvent.

* * * * *